United States Patent
Park et al.

(10) Patent No.: US 9,631,118 B2
(45) Date of Patent: Apr. 25, 2017

(54) ANTI-BACTERIAL AND ANTI-FINGERPRINT COATING COMPOSITION, FILM COMPRISING THE SAME, METHOD OF COATING THE SAME AND ARTICLE COATED WITH THE SAME

(71) Applicant: SAMSUNG ELECTRONICS CO., LTD., Suwon-si, Gyeonggi-do (KR)

(72) Inventors: Byung Ha Park, Suwon-si (KR); Soo Jin Park, Hwaseong-si (KR); Jun Sung Chung, Seongnam-si (KR); In Oh Hwang, Seongnam-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 330 days.

(21) Appl. No.: 14/282,680

(22) Filed: May 20, 2014

(65) Prior Publication Data

US 2014/0370306 A1    Dec. 18, 2014

(30) Foreign Application Priority Data

Jun. 12, 2013   (KR) ........................ 10-2013-0066967

(51) Int. Cl.

| | |
|---|---|
| B32B 9/04 | (2006.01) |
| C09D 179/02 | (2006.01) |
| C09D 5/14 | (2006.01) |
| A01N 25/10 | (2006.01) |
| A01N 59/20 | (2006.01) |
| C07F 7/18 | (2006.01) |
| C08K 5/544 | (2006.01) |
| C08L 101/10 | (2006.01) |

(52) U.S. Cl.
CPC ........... *C09D 179/02* (2013.01); *A01N 25/10* (2013.01); *A01N 59/20* (2013.01); *C07F 7/1836* (2013.01); *C09D 5/14* (2013.01); *C08K 5/544* (2013.01); *C08L 101/10* (2013.01); *Y10T 428/31663* (2015.04)

(58) Field of Classification Search
CPC . C09D 179/02; C09D 5/14; Y10T 428/31663; C08K 5/544; C08L 101/10
USPC ........................................................ 428/447
See application file for complete search history.

(56) References Cited

U.S. PATENT DOCUMENTS

| | | | |
|---|---|---|---|
| 2008/0161268 | A1 | 7/2008 | Yen et al. |
| 2008/0181862 | A1* | 7/2008 | Chisholm .............. A01N 33/12 |
| | | | 424/78.37 |
| 2012/0070481 | A1 | 3/2012 | Bolkan et al. |

FOREIGN PATENT DOCUMENTS

| | | |
|---|---|---|
| EP | 0556518 A2 | 8/1993 |
| EP | 2474577 A1 | 7/2012 |
| WO | 2011/149998 A1 | 12/2011 |

OTHER PUBLICATIONS

STIC Search Report dated Jun. 3, 2016.*

(Continued)

*Primary Examiner* — Eisa Elhilo
(74) *Attorney, Agent, or Firm* — Staas & Halsey LLP (57) ABSTRACT

Disclosed is an anti-bacterial and anti-fingerprint coating composition for forming a multi-functional coating layer having both anti-bacterial functions and anti-fingerprint functions on surfaces of touchscreens provided in portable terminals such as cellular phones, of panels or the like, provided in display devices such as liquid crystal displays (LCDs) or plasma display panels (PDPs), by a dry deposition method.

20 Claims, 9 Drawing Sheets

(56) References Cited

OTHER PUBLICATIONS

Partial European Search Report dated Nov. 7, 2014 in corresponding European Patent Application No. 14170622.6.
"Methoxyethoxyundecyltrimethoxysilane—SIM6491.7", Gelest, Inc., Material Safety Data Sheet, issued Nov. 28, 2011, 3 pages, URL:http://www.gelest.de/gelest/forms/GeneralPages/new_prod_list.aspx?pltype=100.
Wu et al., "Preparation of the non-leaching bactericidal materials containing macromolecular quaternary ammonium salts", Chemical Abstracts Service, XP-002729783, Jan. 2009, pp. 1-2.
Notice of Allowance mailed Feb. 24, 2016 in c European Patent Application No. 14 170 622.6.

\* cited by examiner

ANTI-BACTERIAL AND ANTI-FINGERPRINT COATING COMPOSITION, FILM COMPRISING THE SAME, METHOD OF COATING THE SAME AND ARTICLE COATED WITH THE SAME

CROSS-REFERENCE TO RELATED APPLICATIONS

This application claims the benefit of Korean Patent Application No. 10-2013-0066967, filed on Jun. 12, 2013, in the Korean Intellectual Property Office, the disclosure of which is incorporated herein by reference.

BACKGROUND

1. Field

Embodiments of the present disclosure relate to an anti-bacterial and anti-fingerprint coating composition for forming a multi-functional coating layer having both anti-bacterial functions and anti-fingerprint functions on a surface of a panel or the like, provided in a display device, a film comprising the coating composition, a method for coating the same and an article coated with the same.

2. Description of the Related Art

Generally used mono-functional coating layers include anti-glare (AG) coating, invisible-fingerprint (IF) coating and anti-fingerprint (AF) coating.

AG coating is a method of forming fine irregularities on a panel surface to reduce scattered reflection and thereby obtain anti-fingerprint effects. IF coating is a method of spreading a fingerprint component during fingerprint adhesion to reduce scattered reflection and thereby obtain anti-fingerprint effects. AF coating is a method of forming a coating layer on the surface of a panel by spraying or deposition to provide easy cleaning and improve slip sensation.

In particular, in accordance with the IF coating and AF coating methods, mono-functionality is provided by depositing silicon dioxide ($SiO_2$) on the surface of an article to be coated by vacuum deposition using an electron beam and forming an IF or AF coating layer thereon in order to improve wear resistance.

SUMMARY

Smartphones are operated by touch while being always hold by hand, and are readily stained with cosmetics or oils present on the face and are thus readily exposed to pathogenic bacteria.

Consequently, cosmetics, oils, hand stains and the like attached to heated screens provide an environment facilitating growth and propagation of pathogenic bacteria, thus causing skin troubles and diseases of users via *Escherichia coli* and *staphylococcus*. It may be necessary to prevent such contaminated environment, for children or users having weak antibody.

Therefore, it is one aspect to provide a single coating composition having an anti-bacterial property as well as an anti-fingerprint property, to inhibit propagation of bacteria and kill bacteria when a surface is contaminated with microbes.

In addition, it is one aspect to provide a blend coating composition to which a metal-type anti-bacterial agent having anti-bacterial and anti-fingerprint properties is added.

Additional aspects will be set forth in part in the description which follows and, in part, will be obvious from the description, or may be learned by practice of the invention.

In accordance with one aspect, a coating composition including a quaternary ammonium silane compound includes a group (referred to herein as an "Ra group") represented by a formula of $-[R_2(OCH_2CH_2)_mOR_1]$, wherein $R_1$ includes at least one selected from the group consisting of hydrogen and a C1-C3 alkyl group, $R_2$ includes at least one selected from the group consisting of a C5-C20 alkylene group, a C5-C20 alkenylene group, a C5-C20 alkynylene group, a C5-C20 arylene group, a C6-C20 aryl-alkylene group, a C5-C20 cyclic alkylene group and a C5-C20 alkylene group containing a heteroatom, and m is an integer of 1 to 12, and a silane group represented by a formula of $-[SiX_pY_q]$, wherein X includes at least one selected from the group consisting of a C1-C3 alkyl group, Y includes at least one selected from the group consisting of a halogen atom, a methoxy group and an ethoxy group, p is 0, 1 or 2, q is 1, 2, or 3, and p+q is 3.

The quaternary ammonium silane compound may have a molecular weight of 800 or more.

In accordance with one aspect, a coating composition includes a silane compound represented by a formula of $R_1·O-(CH_2CH_2O)_{m'}-R_{2'}-SiX'_{p'}Y'_{q'}$, wherein $R_1$ includes at least one selected from the group consisting of hydrogen and a C1-C3 alkyl group, $R_2$ comprises at least one selected from the group consisting of a C5-C20 alkylene group, a C5-C20 alkenylene group, a C5-C20 alkynylene group, a C5-C20 arylene group, a C6-C20 aryl-alkylene group, a C5-C20 cyclic alkylene group and a C5-C20 alkylene group containing a heteroatom, X' includes at least one selected from the group consisting of a C1-C3 alkyl group, Y' includes at least one selected from the group consisting of a halogen atom, a C1-C8 alkoxy group and a hydroxyl group, m' is an integer of 1 to 12, p' is 0, 1 or 2, and p'+q' is 3, and an anti-bacterial metal complex.

The anti-bacterial metal complex may include a metal including Ag, Cu, Zn or Pt, metal oxide including AgO, CuO, ZnO or PtO, or a metal-containing inorganic carrier in which a porous carrier including zeolite, phosphate or silica contains a metal.

In accordance with one aspect, an anti-bacterial and anti-fingerprint film formed by coating a surface of a substrate with the coating composition is provided.

The film may have a contact angle to water ($H_2O$), of about 65 degrees or more, and a contact angle to diiodomethane, of about 50 degrees or less.

In accordance with one aspect, a quaternary ammonium silane compound includes an Ra group represented by a formula of $-[R_2(OCH_2CH_2)_mOR_1]$, wherein $R_1$ includes at least one selected from the group consisting of hydrogen and a C1-C3 alkyl group, $R_2$ includes at least one selected from the group consisting of a C5-C20 alkylene group, a C5-C20 alkenylene group, a C5-C20 alkynylene group, a C5-C20 arylene group, a C6-C20 aryl-alkylene group, a C5-C20 cyclic alkylene group, and a C5-C20 alkylene group containing a heteroatom, and m is an integer of 1 to 12, and a silane group represented by a formula of $-[SiX_pY_q]$, wherein X includes at least one selected from the group consisting of a C1-C3 alkyl group, Y includes at least one selected from the group consisting of a halogen atom, a C1-C3 alkoxy group and a hydroxyl group, p is 0, 1 or 2, and p+q is 3.

The quaternary ammonium silane compound may have the following Formula 1 below:

[Formula 1]

wherein m is an integer of 1 to 12 and n is an integer of 1 or more.

The quaternary ammonium silane compound may have a molecular weight of about 800 or more.

In accordance with one aspect, a coating method includes loading an object to be coated in a vacuum chamber, forming a primer layer on the object using silicon dioxide ($SiO_2$), and depositing the coating composition according to any one of claims 1 to 3 on a surface of the primer layer.

The coating method may further include removing foreign matter present on the object, before formation of the primer layer on the object.

In accordance with one aspect, an article surface-coated with an anti-bacterial and anti-fingerprint film including the anti-bacterial and anti-fingerprint coating composition is provided.

The article may be a display, a touch panel or an information terminal.

BRIEF DESCRIPTION OF THE DRAWINGS

These and/or other aspects will become apparent and more readily appreciated from the following description of the embodiments, taken in conjunction with the accompanying drawings of which.

DETAILED DESCRIPTION

Reference will now be made in detail to the embodiments, examples of which are illustrated in the accompanying drawings, wherein like reference numerals refer to the like elements throughout. The embodiments are described below to explain the present invention by referring to the figures.

Hereinafter, embodiments will be described with reference to the accompanying drawings.

An embodiment provides a coating composition, more specifically, a coating composition having an anti-bacterial property as well as an anti-fingerprint property, to inhibit propagation of bacteria and kill bacteria when a surface is contained with microbes.

The coating composition according to one embodiment comprises a composition having a structure represented by Formula 1:

(Formula 1)

That is, a quaternary ammonium silane coating composition exhibiting both anti-bacterial properties and anti-fingerprint properties is provided by introducing an anti-fingerprint group and a silane group into a polyethylene imine (PEI) polymer.

In Formula 1, $R_1$ is selected from hydrogen and a C1-C3 alkyl group, and the C1-C3 alkyl group may be substituted or un-substituted.

In addition, in Formula 1, $R_2$ is selected from the group consisting of a C5-C20 alkylene group, a C5-C20 alkenylene group, a C5-C20 alkynylene group, a C5-C20 arylene group, a C6-C20 aryl-alkylene group, a C5-C20 cyclic alkyl group and a C5-C20 alkylene group containing a heteroatom. These substituent groups may be substituted or un-substituted.

In addition, in Formula 1, m is an integer of 1 to 12 and n is an integer of 1 or more.

In addition, in Formula 1, X is a C1-C3 alkyl group which may be substituted or un-substituted, Y is selected from the group consisting of a halogen atom such as Cl, Br or I, a C1-C8 alkoxy group and a hydroxyl group, p is 0, 1 or 2, and p+q is 3.

In addition, it is possible to obtain a compound suited to form a film on the surface of a substrate, when a molecular weight of the silane compound is 800 or more.

Silane is a type of silicon hydride, whose formula is represented by $Si_nH_{2n+2}$. A silane compound means a compound in which at least one hydrogen of $Si_nH_{2n+2}$ is substituted by another group. Compounds with various properties may be obtained depending on type of substituent group.

The silane compound of Formula 1 has an anti-fingerprint property due to the Ra group (—[$R_2$—($OCH_2CH_2$)$_m$—$OR_1$]), an anti-bacterial property due to the quaternary ammonium polymer (—[$N^+$—($C_2H_4$)]$_n$—), and an adhesion property to the substrate due to the silane group (—[$SiX_pY_q$]). That is, superior anti-fingerprint properties and excellent anti-bacterial properties are obtained when the surface of the substrate is coated with the silane compound of Formula 1.

Figure 1:
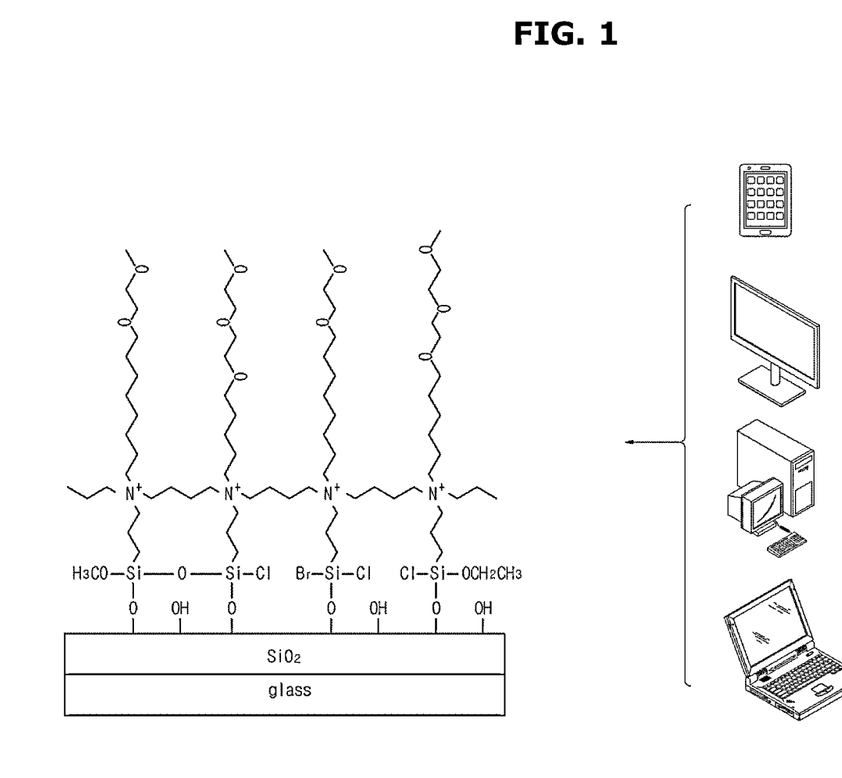
FIG. 1 illustrates a structure in which a substrate is surface-coated by a dry deposition method with a silane compound according to one embodiment.

FIG. 1 illustrates a structure in which a substrate is surface-coated with the silane compound according to one embodiment.

As shown in FIG. 1, when a film is formed by coating a surface of a substrate such as a TV screen, a desktop or notebook monitor screen, a screen of mobile appliance including cellular phone or PDA, or a touch panel of electronic products with the silane compound containing the Ra group (—[$R_2$—($OCH_2CH_2$)$_m$—$OR_1$]) and the quaternary ammonium polymer (—[$N^+$—($C_2H_4$)]$_n$—), the Ra group (—[$R_2$—($OCH_2CH_2$)$_m$—$OR_1$]) is disposed outside from the substrate surface and directly contacts fingerprints, and the quaternary ammonium polymer (—[$N^+$—($C_2H_4$)]$_n$—) is disposed between the Ra group (—[$R_2$—($OCH_2CH_2$)$_m$—$OR_1$]) and the substrate surface.

In addition, the silane group (—[$SiX_pY_q$]) functions to facilitate an adhesion (anchoring) through siloxane bonding to an —OH group of silicon dioxide ($SiO_2$) used as a primer layer. Y comprises at least one selected from a halogen atom such as Cl, Br or I, a C1-C8 alkoxy group and a hydroxyl group. In consideration of reactivity, Y may be a C1 methoxy group (—$OCH_3$).

An anti-fingerprint coating function is quantified by analyzing a water ($H_2O$) contact angle of 60 degrees or more, and a diiodomethane contact angle of 45 degrees or less and this will be described in more detail.

Figure 2A:
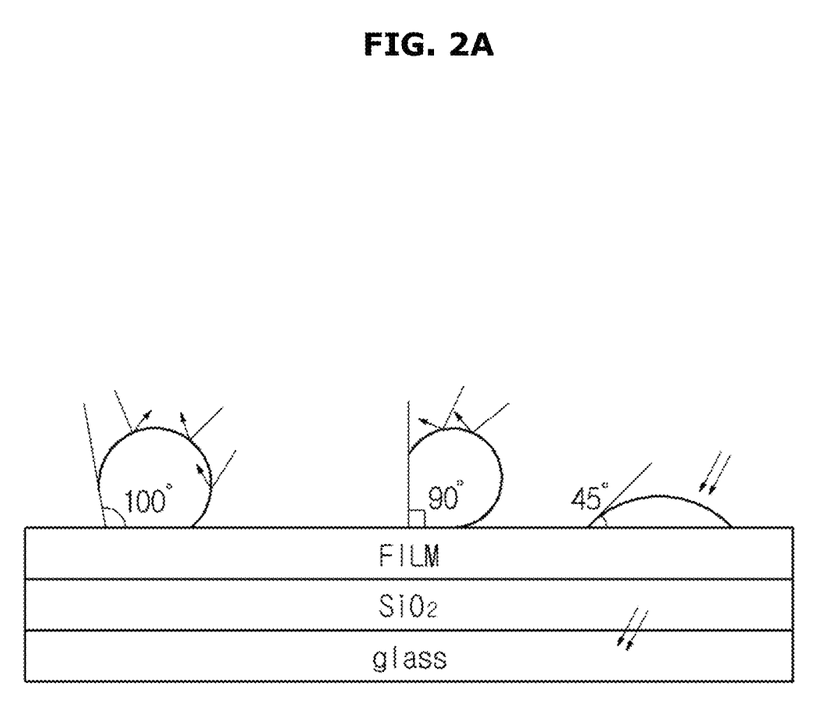
FIG. 2A illustrates contact angles and light reflection patterns on a film according to type of liquid for describing a concept of a contact angle.

FIG. 2A illustrates contact angles and light reflection patterns on a film according to type of liquid for describing a concept of a contact angle.

A contact angle means a predetermined angle that is formed with a solid surface and a liquid surface when a liquid droplet maintains a predetermined lens shape on the horizontal surface of the solid, and the value thereof depends on type of liquid and solid.

As shown in FIG. 2A, it is generally thought that a liquid maintains a droplet form on a solid surface and does not wet the solid surface when a contact angle is greater than 90 degrees, and a liquid spreads and wets the solid surface when a contact angle is less than 90 degrees.

As shown in FIG. 2A, when light is emitted to water ($H_2O$) and diiodomethane having a great contact angle, attached to a film formed on the substrate surface, diffused reflection occurs and these substances are readily visible to an observer. Accordingly, fingerprint components containing water ($H_2O$) and diiodomethane are readily visible and look dirty, when they are attached to film surfaces.

Figure 2B:
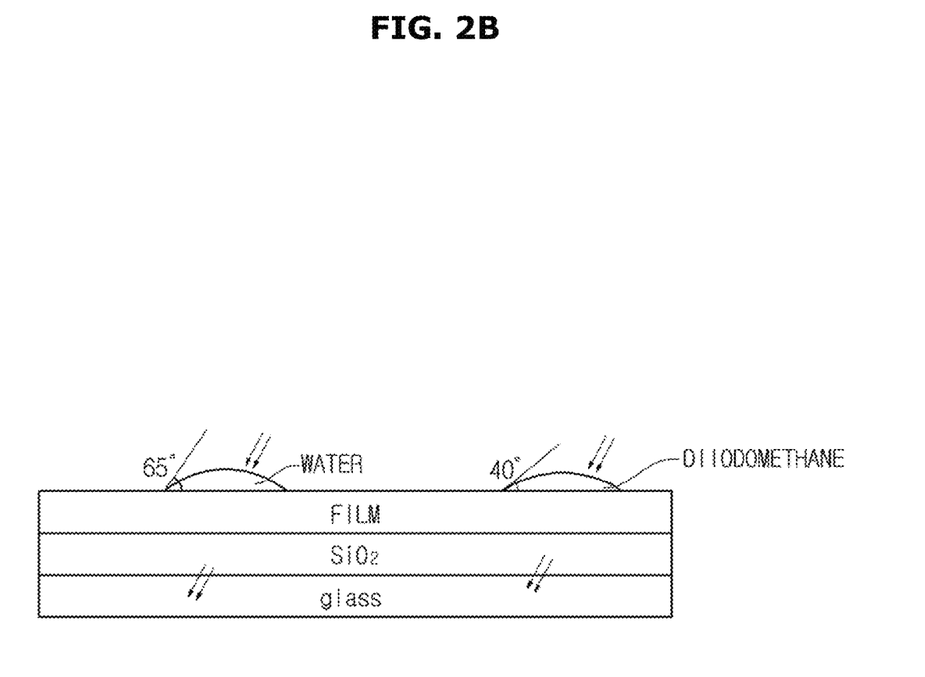
FIG. 2B illustrates contact angles and light reflection patterns, when water ($H_2O$) and diiodomethane are attached to a surface of the film containing the coating composition according to one embodiment.

FIG. 2B illustrates contact angles and light reflection patterns, when water ($H_2O$) and diiodomethane are attached to the surface of the film containing the coating composition according to one embodiment of the present invention.

The coating composition according to one embodiment is the silane compound of Formula 1 and Ra group (—[$R_2$—($OCH_2CH_2$)$_m$—$OR_1$]) is disposed outside and contacts fingerprints, when the film is formed by coating the substrate surface with the composition, as described above. In this case, a contact angle of the Ra group (—[$R_2$—($OCH_2CH_2$)$_m$—$OR_1$]) to water ($H_2O$) is 65 degrees and a contact angle of the Ra group (—[$R_2$—($OCH_2CH_2$)$_m$—$OR_1$]) to diiodomethane is 40 degrees.

Accordingly, as shown in FIG. 2B, water ($H_2O$) or diiodomethane attached to the film surface widely spreads, and when light is emitted thereto, most of the light passes through the substrate, instead of being reflected.

Consequently, although fingerprints containing water ($H_2O$) and diiodomethane are attached to the film, they thinly spread on the film surface and are not readily visible and do not look dirty.

Figure 3A:
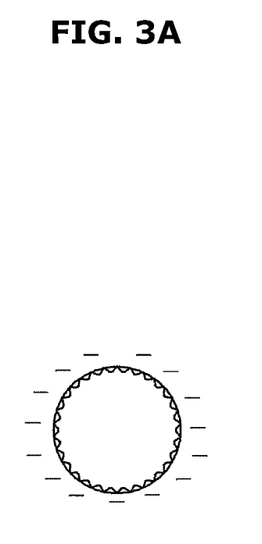
FIG. 3A illustrates *Escherichia coli* as a well-known strain.
Figure 3B:
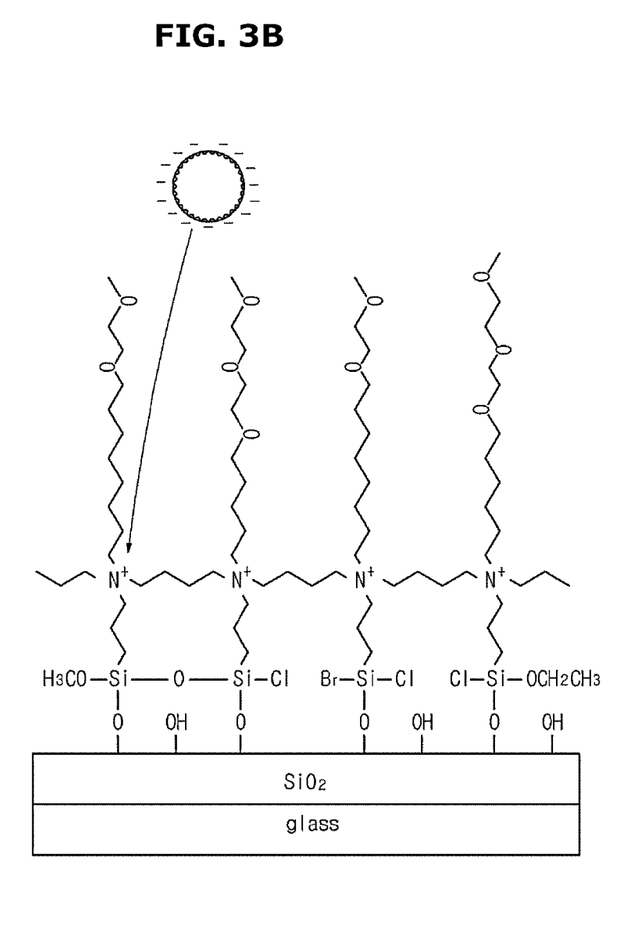
FIG. 3B illustrates a process in which *Escherichia coli* having a negative-charged surface is attracted toward the film due to positive charge (+) of quaternary ammonium.
Figure 3C:
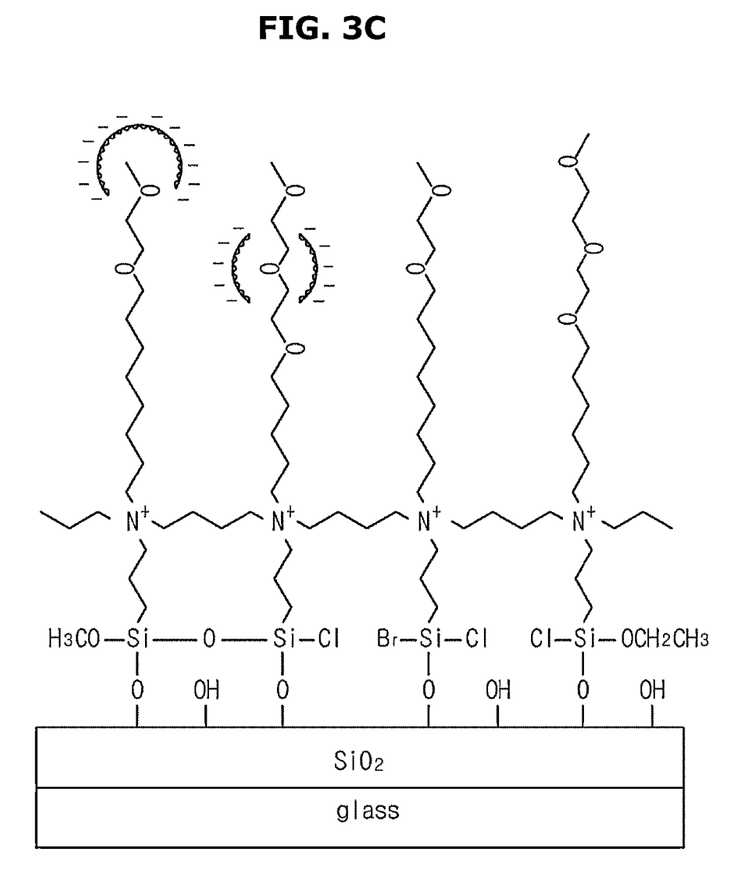
FIG. 3C illustrates a mechanism in which the *Escherichia coli* is killed by the Ra group (—[$R_2$—($OCH_2CH_2$)$_m$—$OR_1$]) present on the film surface.

FIG. 3A illustrates *Escherichia coli* (Gram−) as a well-known strain for description of a principle of imparting an anti-bacterial coating function to a film surface containing the coating composition according to one embodiment. FIGS. 3B and 3C illustrate a process for killing the *Escherichia coli* (Gram−) illustrated in FIG. 3A.

As shown in FIG. 3A, the well-known strain, the *Escherichia coli* (Gram−) has a negative-charged (−) surface. As shown in 3B, when the *Escherichia coli* is attached to a film containing the quaternary ammonium polymer (—[$N^+$—($C_2H_4$)]$_n$—), electrostatic attraction between a positive charge (+) of the quaternary ammonium and a negative charge (−) of *Escherichia coli* (Gram−) is created. Based on the electrostatic attraction, the *Escherichia coli* (Gram−) is attracted toward the film. As shown in FIG. 3C, the attracted *Escherichia coli* (Gram−) physically contacts the Ra group (—[$R_2$—($OCH_2CH_2$)$_m$—$OR_1$]) disposed between the quaternary ammonium polymer (—[$N^+$—($C_2H_4$)]$_n$—) and the *Escherichia coli* (Gram−), thereby resulting in a bacteria killing mechanism.

Through this process, bacteria attached to films are killed, propagation thereof is inhibited, and an anti-bacterial coating function is imparted to the film surface.

Hereinafter, one embodiment will be described in detail.

The coating composition according to another embodiment comprises a composition represented by Formula 2 below:

$$R_{1'}O-(CH_2CH_2O)_{m'}-R_{2'}-SiX'_{p'}Y'_{q'} \quad \text{(Formula 2)}$$

That is, anti-fingerprint and anti-bacterial properties are simultaneously obtained by adding an anti-bacterial metal having an anti-bacterial property to the anti-fingerprint coating composition.

In Formula 2, $R_{1'}$ is selected from the group consisting of hydrogen and a C1-C3 alkyl group, wherein the alkyl group is substituted or un-substituted.

In addition, in Formula 2, $R_{2'}$ is selected from the group consisting of a C5-C20 alkylene group, a C5-C20 alkenylene group, a C5-C20 alkynylene group, a C5-C20 arylene group, a C6-C20 aryl-alkylene group, a C5-C20 cyclic alkyl group and a C5-C20 alkylene group containing a heteroatom. These substituent groups may be substituted or un-substituted.

In addition, in Formula 2, m' is an integer of 1 to 12.

In addition, in Formula 2, X' is a C1-C3 alkyl group which may be substituted or un-substituted, Y' is selected from a halogen atom such as Cl, Br or I, a C1-C8 alkoxy group and a hydroxyl group, p' is 0, 1, or 2, and p'+q' is 3.

A metal complex includes a metal such as Ag, Cu, Zn or Pt, metal oxide such as AgO, CuO, ZnO or PtO, and a metal-containing inorganic carrier in which a porous carrier such as zeolite, phosphate or silica contains a metal.

The metal complex has an anti-bacterial function and a metal complex is dispersed in an anti-fingerprint coating sol to constitute a coating composition.

Hereinafter, a process of forming a film by coating a substrate surface with the coating composition according to the embodiment will be described with reference to FIG. 4. The process of forming the film may be a wet process or a dry process, formation of the film using the dry process may be further advantageous and the dry process will thus be described below.

Figure 4:
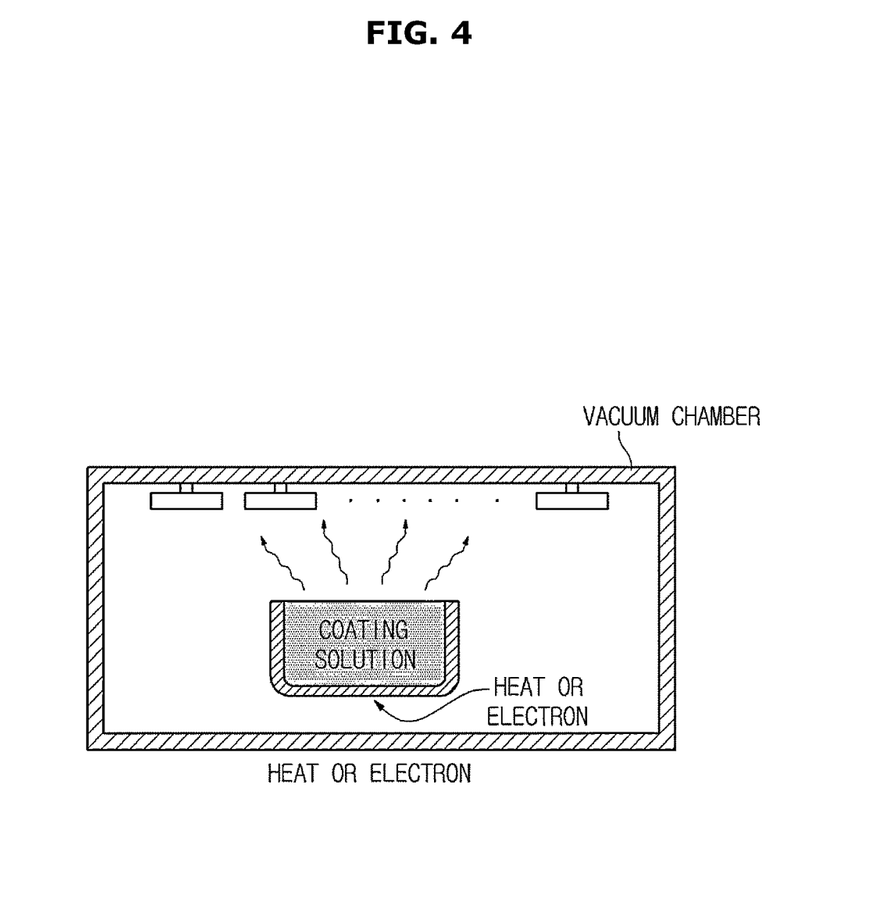
FIG. 4 illustrates a vacuum deposition process of forming a film on a display portion or a touch panel of an electronic product.

As shown in FIG. 4, vacuum deposition may be used as the dry process of forming the film on a display portion or a touch panel of an electronic product.

Vacuum deposition means a method of forming a thin film on an opposite surface facing an evaporation source by evaporating a metal or compound under vacuum. An example of the vacuum deposition process is given as follows. A substrate is mounted on the ceiling of a vacuum chamber such that the surface thereof to be coated faces downward, and a bath containing a coating solution is placed on the chamber bottom facing the substrate. When heat or an electron beam is applied to the bath to evaporate the coating solution, the evaporated coating solution is deposited on the surface of the substrate mounted on the ceiling to form a thin film.

The example of the vacuum deposition process according to the embodiment includes removing foreign matter, primarily depositing silicon dioxide ($SiO_2$) as a primer layer, and secondarily depositing an anti-bacterial and anti-fingerprint coating film.

More specifically, the removal of the foreign matter involves removing the foreign matter present on a surface of an article to be coated. The article to be coated is placed on a jig, is fixed using a magnetic and foreign matter or water attached to the product surface is removed using an ion gun. In addition, the product surface is activated in order to facilitate deposition. The removal of the foreign matter may be omitted, if appropriate.

Next, in accordance with primary deposition, silicon dioxide ($SiO_2$) as a primer layer is formed on a surface of an article to be coated in which foreign matter is removed and the surface is activated using electron beam irradiation. More specifically, first, a substrate is mounted on the ceiling of a vacuum chamber such that a surface of the substrate to be coated faces downward, a bath containing a coating solution is placed on the chamber bottom facing the substrate, deposition conditions including deposition thickness are set and a vacuum deposition device is operated. At this time, an electron beam is applied to silicon dioxide ($SiO_2$) and the silicon dioxide ($SiO_2$) is evaporated. The evaporated silicon dioxide ($SiO_2$) is deposited on the surface of the substrate to form a silicon dioxide ($SiO_2$) film as a primer layer.

It is difficult to attach a silane group to a glass as a substrate since the glass has no —OH group. Accordingly, —OH group is produced by forming the silicon dioxide ($SiO_2$) film and the silane group is effectively deposited during secondary deposition.

Next, in secondary deposition, an anti-bacterial and anti-fingerprint coating layer is formed on the primer layer using a coating composition containing silicon. A detailed explanation of the coating layer formation is the same as that of the primer layer formation and overlapping contents are thus omitted.

A boiling point of the coating composition of the present embodiment depends on the Ra group (—[$R_2$—($OCH_2CH_2$)$_m$—$OR_1$]). For this reason, when a film is formed by vacuum deposition, heat or electron beam level is determined in consideration of the boiling point of the coating composition.

Hereinafter, Comparative Examples and Test Examples of the coating composition according to the embodiment will be described in detail.

Preparation Example 1

Coating composition comprising methoxyethoxyundecyldimethyl(3-trimethoxysilyl propyl)ammonium iodide polyethyleneimine Comparative Example 1

Coating Composition Comprising Methoxyethoxyundecyltrimethoxysilane

Comparative Example 2

Coating composition comprising octadecyldimethyl(3-trimethoxysilylpropyl)ammonium chloride Comparative Example 3

Coating composition comprising methoxyethoxyundecyldimethyl(3-trimethoxysilylpropyl)ammonium chloride The coating composition of Preparation Example 1 and coating compositions of Comparative Examples 1, 2 and 3 are shown in Table 1 below.

TABLE 1

| | Coating material | Coating type |
|---|---|---|
| Comparative Example 1 | [structure] | IF coating (Invisible Fingerprint) |
| Comparative Example 2 | [structure] | Anti-bacterial coating |
| Comparative Example 3 | [structure] | Anti-fingerprint anti-bacterial coating (monomer) |

TABLE 1-continued

| | Coating material | Coating type |
|---|---|---|
| Preparation Example 1 | $R_2(OCH_2CH_2)mOR_1$ — $[N^+]_n$ — $SiX_pY_q$ (polymer structure) | Anti-fingerprint anti-bacterial coating (polymer) |

As is seen from Table 1, the silane coating composition of Comparative Example 1 has an anti-fingerprint function since it contains methoxy and ethoxy groups, but has no anti-bacterial function.

The silane coating composition of Comparative Example 2 has no anti-fingerprint function since it contains no methoxy and ethoxy groups, but has an anti-bacterial function, since it contains quaternary ammonium.

Silane coating compositions of Comparative Example 3 and Preparation Example 1 have anti-fingerprint function since they contain methoxy and ethoxy groups, and they have anti-bacterial function, since they contain quaternary ammonium.

Hereinafter, Test Examples related to anti-fingerprint function and anti-bacterial function obtained when a film is formed on a surface of a touch panel substrate of a smartphone using the coating composition prepared in Preparation Example 1 and the results are described.

Test Example 1

Contact angles of water ($H_2O$) and diiodomethane attached to a film surface formed using the coating composition of Preparation Example 1 and contact angles of water ($H_2O$) and diiodomethane attached to film surfaces formed using the coating compositions of Comparative Examples 1, 2 and 3 were measured.

Test Example 2

A bacteria decrease proportion of the film formed using the coating composition of Preparation Example 1 and bacteria decrease proportions of films formed using the coating compositions of Comparative Examples 1, 2 and 3 are measured.

Test Example 3

A bacteria removal proportion of the film formed using the coating composition of Preparation Example 1 and bacteria removal proportions of films formed using the coating compositions of Comparative Examples 1, 2 and 3 are measured.

Results of Test Examples 1 to 3 are shown in Table 2 below.

TABLE 2

| | | Comparative Example 1 | Comparative Example 2 | Comparative Example 3 | Preparation Example 1 |
|---|---|---|---|---|---|
| | | Coating type | | | |
| | | IF coating (Invisible fingerprint) | Anti-bacterial coating | Anti-fingerprint anti-bacterial coating (monomer) | Anti-fingerprint anti-bacterial coating (polymer) |
| Anti-fingerprint property | Contact angle (DI/DM) | OK (75/45) | NG (93/57) | OK (72/42) | OK (65/40) |
| Anti-bacterial property | Bacteria decrease proportion (%) | 68 | 64 | 76 | 99 |
| | Bacteria removal proportion (%) | NG | NG | NG | 84 |

Considering anti-fingerprint property results, as is seen from Table 2, the film formed using the coating composition of Comparative Example 2 has a contact angle to water ($H_2O$) of 93 degrees and a contact angle to diiodomethane of 57 degrees, and a film formed using the coating composition of Comparative Example 3 has a contact angle to water ($H_2O$) of 72 degrees and a contact angle to diiodomethane of 42 degrees. For this reason, when light is emitted to the films, diffused reflection occurs and fingerprints attached to the film surface are readily visible by a viewer.

On the other hand, the film formed using the coating composition of Comparative Example 1 has a contact angle to water ($H_2O$) of 75 degrees and a contact angle to diiodomethane of 45 degrees, and the film formed using the coating composition of Preparation Example 1 has a contact angle to water ($H_2O$) of 65 degrees, and a contact angle to diiodomethane of 40 degrees. When fingerprints are attached to films, they thinly spread, diffused reflection of light is decreased, they are not readily visible and anti-fingerprint property is improved.

Considering bacteria decrease proportion, Comparative Examples 1, 2 and 3, and Preparation Example 1 have bacteria decrease proportions of 68%, 64%, 76% and 99%, respectively. Accordingly, the film formed using the coating composition according to the embodiment of the present invention exhibits superior bacteria decrease proportion.

Considering bacteria removal proportion, Comparative Examples 1, 2 and 3 have no bacteria removal function, but Preparation Example 1 has a bacteria removal proportion of 84%. Accordingly, the film formed using the coating composition according to the embodiment of the present invention exhibits superior bacteria removal proportion.

Hereinafter, Preparation Examples and Examples of coating compositions according to another embodiment will be described.

Preparation Example 2

Coating composition obtained by dispersing 200 nm CuO particles in a methoxyethoxyundecyltrimethoxysilane sol at a concentration of 1%.

Test Example 4

A sample coated with the coating composition of Preparation Example 2 is inoculated with bacteria and then incubated for 24 hours, and a bacteria removal proportion is measured.

Figure 5:
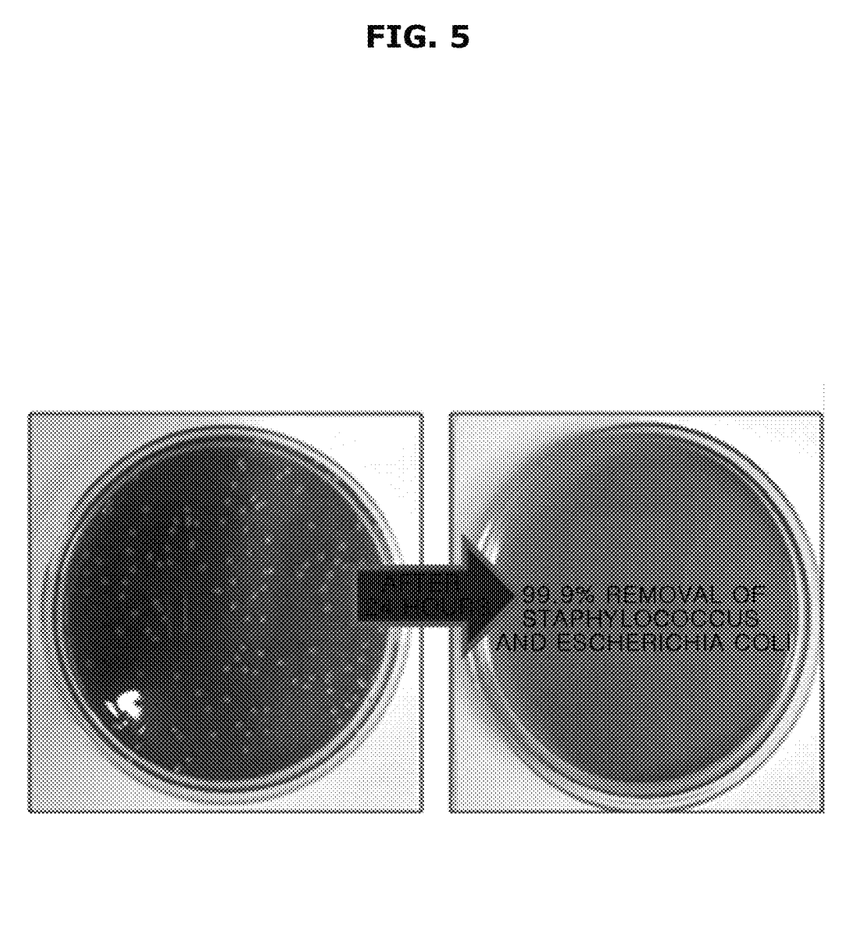
FIG. 5 is an image of colony of viable bacteria after incubation according to Test Example 4.

FIG. 5 is an image of colony of viable bacteria after incubation according to Test Example 4. As shown in FIG. 5, the coating composition according to Preparation Example 2 exhibits the number of viable bacteria, of 10 or less and thus bacteria removal proportion of 99.9%. This means that the coating composition according to Preparation Example 2 has higher bacteria removal proportions than Comparative Examples 1, 2 and 3.

Figure 6:
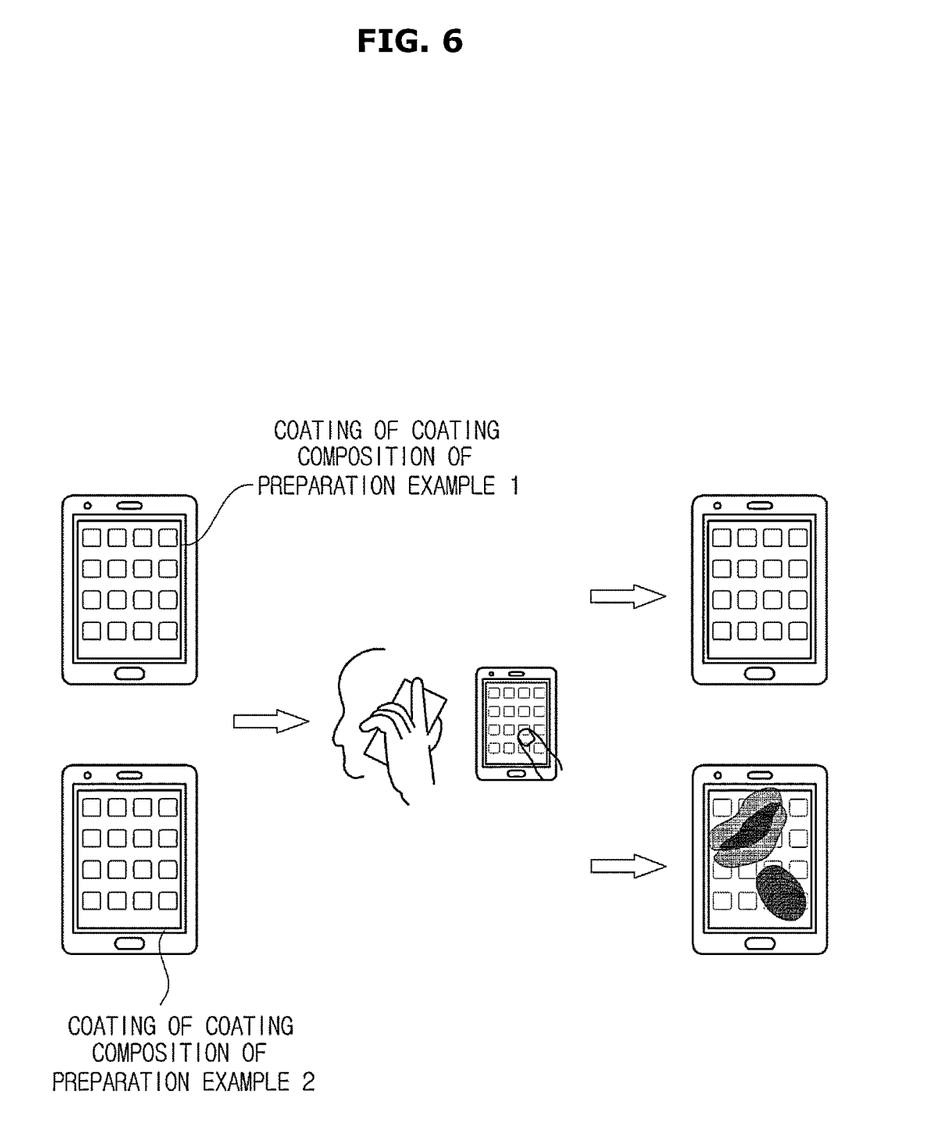
FIG. 6 illustrates comparison of a touch panel of a smartphone using the coating composition according to one embodiment, as the coating composition of Preparation Example 1, with a touch panel of a smartphone using the coating composition of Comparative Example 2.

FIG. 6 illustrates comparison of a touch panel of a smartphone using the coating composition according to one embodiment of the present invention (the coating composition of Preparation Example 1) with a touch panel of a smartphone using the coating composition of Comparative Example 2.

As shown in FIG. 6, illustrates the smartphone using Preparation Example 1 and illustrates the smartphone using Comparative Example 2. Upon calling using a smartphone, a screen of the smartphone contacts the face and is stained with oils or cosmetics. In addition, upon search or message writing using a smartphone, a screen is touched and is thus stained with fingerprints.

As shown in FIG. 6, although the smartphone screen is stained with oils or cosmetics of the face, dirties are not readily visible to the naked eye due to properties of the coating composition of Preparation Example 1. As described above, since the coating composition of Preparation Example 1 has a low contact angle to water ($H_2O$) or diiodomethane, fingerprint or oil components of the face widely spread on the coating film surface and are thus not readily visible to the naked eye.

On the other hand, in the case of the smartphone of FIG. 6 coated with Comparative Example 2, oils and fingerprint components of the face are relatively readily visible to the naked eye and look dirty, since the composition coated on the screen thereof has a large contact angle to water ($H_2O$) or diiodomethane.

Although a few embodiments have been shown and described, it would be appreciated by those skilled in the art that changes may be made in these embodiments without departing from the principles and spirit of the invention, the scope of which is defined in the claims and their equivalents.

What is claimed is:

1. A coating composition comprising a quaternary ammonium silane compound comprising:
   a group represented by a formula of —[$R_2(OCH_2CH_2)_mOR_1$],
   wherein $R_1$ comprises at least one selected from the group consisting of hydrogen and a C1-C3 alkyl group, $R_2$ comprises at least one selected from the group consisting of a C5-C20 alkylene group, a C5-C20 alkenylene group, a C5-C20 alkynylene group, a C5-C20 arylene group, a C6-C20 aryl-alkylene group, a C5-C20 cyclic alkylene group and a C5-C20 alkylene group containing a heteroatom, and m is an integer of 1 to 12; and
   a silane group represented by a formula of —[$SiX_pY_q$],
   wherein X comprises at least one selected from the group consisting of a C1-C3 alkyl group, Y comprises at least one selected from the group consisting of a halogen atom, a methoxy group and an ethoxy group, p is 0, 1 or 2, q is 1, 2, or 3, and p+q is 3.

2. The coating composition according to claim 1, wherein the quaternary ammonium silane compound has a molecular weight of 800 or more.

3. A coating composition comprising:
   a silane compound represented by a formula of $R_1$,O—($CH_2CH_2O$)$_{m'}$—$R_{2'}$—$SiX'_{p'}Y'_{q'}$,
   wherein $R_{1'}$ comprises at least one selected from the group consisting of hydrogen and a C1-C3 alkyl group, $R_{2'}$ comprises at least one selected from the group consisting of a C5-C20 alkylene group, a C5-C20 alkenylene group, a C5-C20 alkynylene group, a C5-C20 arylene group, a C6-C20 aryl-alkylene group, a C5-C20 cyclic alkylene group and a C5-C20 alkylene group containing a heteroatom, X' comprises at least one selected from the group consisting of a C1-C3 alkyl group, Y' comprises at least one selected from the group consisting of a halogen atom, a C1-C8 alkoxy group and a hydroxyl group, m' is an integer of 1 to 12, p' is 0, 1 or 2, q' is 1, 2, or 3, and p'+q' is 3; and
   an anti-bacterial metal complex.

4. The coating composition according to claim 3, wherein the anti-bacterial metal complex comprises a metal including Ag, Cu, Zn or Pt, metal oxide including AgO, CuO, ZnO or PtO, or a metal-containing inorganic carrier in which a porous carrier including zeolite, phosphate or silica contains a metal.

5. An anti-bacterial and anti-fingerprint film formed by coating a surface of a substrate with the coating composition according to claim 1.

6. The anti-bacterial and anti-fingerprint film according to claim 5, wherein the film has a contact angle to water ($H_2O$), of about 65 degrees or more, and a contact angle to diiodomethane, of about 50 degrees or less.

7. A quaternary ammonium silane compound comprising:
   a group represented by a formula of —[$R_2(OCH_2CH_2)_mOR_1$],
   wherein $R_1$ comprises at least one selected from the group consisting of hydrogen and a C1-C3 alkyl group, $R_2$ comprises at least one selected from the group consisting of a C5-C20 alkylene group, a C5-C20 alkenylene group, a C5-C20 alkynylene group, a C5-C20 arylene group, a C6-C20 aryl-alkylene group, a C5-C20 cyclic alkylene group, and a C5-C20 alkylene group containing a heteroatom, and m is an integer of 1 to 12; and a silane group represented by a formula of —[SiX$_p$Y$_q$], wherein X comprises at least one selected from the group consisting of a C1-C3 alkyl group, Y comprises at least one selected from the group consisting of a halogen atom, a C1-C3 alkoxy group and a hydroxyl group, p is 0, 1 or 2, q is 1, 2, or 3, and p+q is 3.

8. The quaternary ammonium silane compound according to claim 7, wherein the quaternary ammonium silane compound has the following Formula 1 below:

[Formula 1]

wherein m is an integer of 1 to 12, n is an integer of 1 or more, p is 0, 1, or 2, and q is 1, 2 or 3.

9. The quaternary ammonium silane compound according to claim 7, wherein the quaternary ammonium silane compound has a molecular weight of about 800 or more.

10. A coating method comprising:
loading an object to be coated in a vacuum chamber;
forming a primer layer on the object using silicon dioxide (SiO$_2$); and
depositing the coating composition according to claim 1 on a surface of the primer layer.

11. The coating method according to claim 10, further comprising removing foreign matter present on the object, before formation of the primer layer on the object.

12. An article surface-coated with an anti-bacterial and anti-fingerprint film comprising the anti-bacterial and anti-fingerprint coating composition according to claim 1.

13. The article according to claim 12, wherein the article is a display, a touch panel or an information terminal.

14. A coating composition for a substrate, comprising:
a quaternary ammonium silane that imparts anti-finger printing properties and anti-bacteria properties to the coated substrate, wherein the quaternary ammonium silane comprises:
a group represented by a formula of —[R$_2$(OCH$_2$CH$_2$)$_m$OR$_1$],
wherein R$_1$ comprises at least one selected from the group consisting of hydrogen and a C1-C3 alkyl group, R$_2$ comprises at least one selected from the group consisting of a C5-C20 alkylene group, a C5-C20 alkenylene group, a C5-C20 alkynylene group, a C5-C20 arylene group, a C6-C20 aryl-alkylene group, a C5-C20 cyclic alkylene group and a C5-C20 alkylene group containing a heteroatom, and m is an integer of 1 to 12, and
a silane group represented by a formula of —[SiX$_p$Y$_q$],
wherein X comprises at least one selected from the group consisting of a C1-C3 alkyl group, Y comprises at least one selected from the group consisting of a halogen atom, a methoxy group and an ethoxy group, p is 0, 1 or 2, g is 1, 2, or 3, and p+q is 3.

15. An anti-bacterial and anti-fingerprint film formed by coating a surface of a substrate with the coating composition according to claim 2.

16. An anti-bacterial and anti-fingerprint film formed by coating a surface of a substrate with the coating composition according to claim 3.

17. A coating method comprising:
loading an object to be coated in a vacuum chamber;
forming a primer layer on the object using silicon dioxide (SiO$_2$); and
depositing the coating composition according to claim 2 on a surface of the primer layer.

18. A coating method comprising:
loading an object to be coated in a vacuum chamber;
forming a primer layer on the object using silicon dioxide (SiO$_2$); and
depositing the coating composition according to claim 3 on a surface of the primer layer.

19. An article surface-coated with an anti-bacterial and anti-fingerprint film comprising the anti-bacterial and anti-fingerprint coating composition according to claim 2.

20. An article surface-coated with an anti-bacterial and anti-fingerprint film comprising the anti-bacterial and anti-fingerprint coating composition according to claim 3.

* * * * *